US00PP31190P2

(12) United States Plant Patent
Bedard

(10) Patent No.: US PP31,190 P2
(45) Date of Patent: Dec. 10, 2019

(54) FLORIBUNDA ROSE PLANT NAMED 'WEKZAZOU'

(50) Latin Name: *Rosa hybrida*
Varietal Denomination: WEKzazou

(71) Applicant: Early Morning, LLC, Pomona, CA (US)

(72) Inventor: Christian Bedard, Rancho Cucamonga, CA (US)

(73) Assignee: Early Morning, LLC, Lawrenceburg, IN (US)

( * ) Notice: Subject to any disclaimer, the term of this patent is extended or adjusted under 35 U.S.C. 154(b) by 0 days.

(21) Appl. No.: 16/350,518

(22) Filed: Nov. 28, 2018

(51) Int. Cl.
*A01H 5/02* (2018.01)
*A01H 6/74* (2018.01)

(52) U.S. Cl.
USPC ..... Plt./141

(58) Field of Classification Search
USPC ..... Plt./141
CPC ..... A01H 5/02; A01H 6/74
See application file for complete search history.

(56) References Cited

U.S. PATENT DOCUMENTS

PP15,076 P2 8/2004 Carruth

OTHER PUBLICATIONS

Weeks Roses, "All Dressed Up", Wholesale Rose Catalog, 86 pages, 2019.

*Primary Examiner* — Annette H Para
(74) *Attorney, Agent, or Firm* — McKee, Voorhees & Sease, PLC

(57) ABSTRACT

A new variety of *Floribunda* rose suitable for garden decoration, having flowers of orangey gold suffused with pink coloration.

1 Drawing Sheet

Classification: The present invention relates to a new *Rosa hybrida* plant.

Variety Denomination: The new plant has the varietal denomination 'WEKzazou'.

BACKGROUND OF THE INVENTION

This invention relates to a new and distinct variety of *Floribunda* Rose. It has as its seed parent the variety known as 'ORAsoglo' (not patented) and as its pollen parent the variety known as Distant Drums (not patented).

SUMMARY OF THE INVENTION

Among the features which distinguish the new variety from other presently available and commercial rose cultivars known to the inventor are the following combinations of characteristics: its very double flowers of orangey gold suffused with pink coloration, its excellent color stability throughout the life of the flowers and its moderate fruity and spice with hints of cinnamon fragrance. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKzazou' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'ORAsoglo' by the following combination of characteristics: whereas 'WEKzazou' bears very double flowers (about 36 to 72 petals) of orangey gold suffused with pink coloration, 'ORAsoglo' bears double flowers of medium yellow coloration with significantly lesser petalage (about 30 to 40 petals). The new variety has an upright moderately spreading medium height growing habit (about 95 to about 140 cm. in height), whereas the seed parent has an upright significantly taller growing habit (about 120 to about 185 cm. in height).

The new variety may be distinguished from its pollen parent, Distant Drums by the following combination of characteristics: whereas 'WEKzazou' bears very double flowers (about 36 to 72 petals) of orangey gold suffused with pink coloration, Distant Drums bears double flowers of tan-mauve blend coloration with significantly lesser petalage (about 40 petals). The new variety has flowers with moderate fruity and spice with hints of cinnamon fragrance, whereas the pollen parent has flowers with strong anise and myrrh fragrance.

COMPARISON WITH THE CLOSEST COMMERCIALLY AVAILABLE CULTIVAR

The new variety may be distinguished from its closest commercially available cultivar, 'WEKscemala' (U.S. Plant Pat. No. 15,076) by the following combination of characteristics: whereas 'WEKzazou' bears very double flowers (about 36 to 72 petals) of orangey gold suffused with pink coloration, 'WEKscemala' bears double flowers of yellow blushed orange-red coloration with significantly lesser petalage (about 22 to 27 petals). The new variety has flowers with moderate fruity and spice with hints of cinnamon fragrance, whereas the closest commercially available cultivar has flowers with a slight tea fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to six or more per stem. Flowers may be borne in regular rounded clusters on strong somewhat short to medium length stems (about 18 to about 42 cm.). The cluster ranges from about 11.5 to about 15.5 cm. in diameter. Outdoors, the plant blooms abundantly and nearly continuously during the growing season. The flowers have a moderate fruity and spice with hints of cinnamon fragrance.

BUD

The peduncle is about 1.9 to about 5.6 cm. in length, of moderately heavy caliper (about 0.3 to about 0.5 cm. in diameter), and usually erect. It is entirely smooth, with few hairs. Peduncle color is between 144A and 146D.

Before the calyx breaks, the bud is about 1.1 to about 1.5 cm. in diameter at the widest point, about 1.4 to about 2.1 cm. in length, and pointed to somewhat ovoid in shape. The surface of the bud bears between 10 to 15 foliaceous appendages and few hairs, usually with slender entire to sometimes much cut foliaceous parts extending beyond the tip of the bud about ¼ or more of its length. Bud color is between 137C and 146D often heavily suffused, especially on the side exposed to the sun, with between 187B and 187A.

The sepals are 5 per flower, about 1.8 to about 3.5 cm. in length and about 0.8 to about 1.2 cm. in width at the widest point. The outer surface color of the sepal is between 137C and 146D often heavily suffused, especially on the side exposed to the sun, with between 187B and 187A. The outer surface of the sepal is smooth and bears between 0 to 8 foliaceous appendages with few hairs. The inner surface color of the sepal is near 146D broadly bordered by near 137C. After the sepals open, the inner surface color is often heavily suffused, especially on the area exposed to the sun, with between 187A and 187B. The inner surface of the sepal is covered with fine wooly tomentum; sepal margins are entire and lined with few stipitate glands and many hairs. The sepals are moderately permanent, and usually straight in shape with acute apices.

The receptacle of the flower is of medium length (about 0.5 to about 1.1 cm.) and moderately heavy in caliper (about 0.9 to about 1.4 cm. in diameter). The receptacle is urn-shaped in form. Its surface is smooth with few hairs and with somewhat thin fleshy walls. The receptacle color is between 144A and 146D.

As the petals open (after the calyx breaks), the bud is about 1.1 to about 2.2 cm. in diameter at the widest point, about 1.8 to about 3.4 cm. in length, and pointed to somewhat ovoid in form. The color of the under surfaces of the newly opened petals is between 22A and 18A often heavily blushed on the outermost petals with between 53B and 53D to as dark as between 53A and 187B. At the point where the petal attaches, there is a somewhat large zone of between 150B and 151D. The color of the upper surfaces of the newly opened petals is between 22A and 16B usually moderately suffused with between 53A and 53B. At the point where the petal attaches, there is a moderately large zone of between 150B and 154A.

BLOOM

When fully open, the bloom ranges from about 6.9 to about 10.8 cm. in diameter. Petalage is very double with about 36 to 72 petals and about 13 to 47 petaloids irregularly arranged. When partially open, the bloom form is somewhat high centered to cupped, and the petals are moderately tightly spiraled to cupped with petal edges moderately reflexed outward. When fully open, the bloom form is more cupped, and the petals are loosely cupped with petal edges moderately reflexed outward.

PETALS

The substance of the petals is moderately heavy and of medium thickness, with upper surfaces moderately satiny and under surfaces slightly shiny to matte. The petals are about 3.0 to about 5.3 cm. in length and about 1.4 to about 4.6 cm. in width at the widest point. Petal margins are entire.

The outer petals are moderately obovate to somewhat rounded in shape with rounded apices.

The inner petals are moderately oblanceolate to somewhat obovate in shape with rounded apices.

Petaloids are about 0.6 to about 3.7 cm. in length and about 0.3 to about 2.5 cm. in width at the widest point. Petaloids are irregularly shaped moderately oblanceolate to somewhat obovate to subulate with rounded apices.

NEWLY OPENED FLOWER

The under surface color of the outer, intermediate and inner petals is between 16C and 22C. There is no visible change in coloration at the point where the petal attaches. The upper surface color of the outer, intermediate and inner petals is between 15B and 16B usually moderately suffused with between 53B and 53D. There is no visible change in coloration at the point where the petal attaches.

The under and upper surface colors of the petaloids are similar in coloration to the upper and under surfaces of the intermediate and inner petals.

The general tonality of the newly opened flower is between 15B and 16B usually moderately suffused with between 53B and 53D.

THREE-DAY-OLD FLOWER

The under surface color of the outer, intermediate and inner petals is between 10B and 22C. There is no visible change in coloration at the point where the petal attaches. The upper surface color of the outer, intermediate and inner petals is between 8B and 16B usually moderately suffused with between 60C and 53D to as dark as between 60A and 60B. There is no visible change in coloration at the point where the petal attaches.

The under and upper surface colors of the petaloids are similar in coloration to the upper and under surfaces of the intermediate and inner petals.

The general tonality of the three-day-old flower is between 8B and 16B usually moderately suffused with between 60C and 53D to as dark as between 60A and 60B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 125) and are arranged regularly about the pistils; a few are mixed with petaloids. The filaments are of medium to somewhat long length (about 0.4 to about 1.4 cm.) most with anthers. Filaments are between 16B and 15C in color usually heavily suffused with between 60A and 53B. The anthers are moderately small for the class and all open approximately at the same time. Anther color when immature is near 20A on the external part and near 8D on the internal part. Anther color at maturity is near 164C on the external part and near 200A on the internal part. Pollen is moderate and between 18B and 19C in color.

FEMALE REPRODUCTIVE ORGANS

Pistils vary in number (average about 105). The styles are moderately uneven, short to average in length (about 0.2 to about 0.6 cm.), somewhat thin to average in caliper, and loosely bunched to somewhat separated. Stigma color is between 20C and 19B. Style color is between 2D and 4D usually heavily suffused with between 187C and 187B. Ovaries are usually all enclosed in the calyx. The ovaries are of small size and between 158B and 158C in color.

Hips have not been observed on this variety when grown in Pomona, Calif.

FOLIAGE

The compound leaves are usually comprised of three to seven leaflets and are borne abundantly. The five-leaflet leaves are about 9.7 to about 13.8 cm. in length and about 8.0 to about 11.8 cm. in width at the widest point, moderately leathery to somewhat crisp in texture on both sides, and glossy in finish on the upper side and somewhat semi-glossy in finish on the under side. The leaves have a pinnate venation pattern. The terminal leaflets are about 4.4 to about 6.8 cm. in length and about 2.6 to about 4.2 cm. in width at the widest point, shaped ovate with acute apices and rounded bases. Their margins are usually simply serrate.

The upper surface color of the mature leaf is between 139A and 147A. The under surface color of the mature leaf is between 147B and 146A. The under and upper colors of the leaf veins on the mature leaf are similar in coloration to the upper and under surfaces colors of the mature leaf. The upper surface color of the-young leaf is between 137B and 146A, often heavily suffused with near 187B. The under-surface color of the young leaf is between 139C and 138B, often heavily suffused with between 187B and 187C. The under and upper colors of the leaf veins on the young leaf are similar in coloration to the upper and under surfaces colors of the young leaf.

The rachis is about 5.5 to about 7.8 cm. in length, about 0.1 to about 0.15 cm in width at the widest point, and moderately rough. The upper side is deeply grooved with few hairs and stipitate glands on the edges of the grooves. The under side of the rachis is moderately rough with few stipitate glands and small prickles. The rachis color is near 146D on the underside and near 137B on the upper side, often heavily suffused on the young leaves with between 187B and 187C.

The stipules are about 1.4 to about 2.5 cm. in length and of medium width (about 0.4 to about 0.6 cm.) with medium length straight points that usually turn out at an angle of more than 45 degrees. The under and upper surface color of the stipule is between 137B and 137C. The upper and under surfaces of the stipules are smooth in texture.

The petiole is somewhat light to average in caliper and moderately rough. The upper side is deeply grooved with few hairs and stipitate glands on the edges of the grooves. The under side of the petiole is moderately rough with few stipitate glands and small prickles. The petiole is about 0.7 to about 1.3 cm. in length and about 0.1 to about 0.15 cm in width at the widest point. The petiole color is near 146D on the underside and near 137B on the upper side, often heavily suffused on the young leaves with between 187B and 187C.

The plant displays an average degree of resistance to powdery mildew (*Sphaerotheca pannosa*), downy mildew (*Peronospora sparsa*) and rust (*Phragmidium* sp.) as compared to other commercial varieties grown under comparable conditions in Pomona, Calif. The plant's winter hardiness and drought/heat tolerance are yet to be determined.

GROWTH

The plant has an upright moderately spreading medium height growing habit (about 95 to about 140 cm. in height and about 122 to about 176 cm. spread at the widest point), with full branching. It displays moderately vigorous growth and the canes are of medium caliper for the class (about 1.5 to about 2.0 cm. in diameter at the widest point).

The color of the major stems is between 146A and 146B. The major stems are rough in texture and they bear many large prickles that are about 1.1 to about 1.8 cm. in length. The large prickles are angled slightly downward with a long narrow oval base; prickle color is between 165B and 164A often lightly suffused with near 201C. The major stem bears some small prickles of similar shape and coloration.

The color of the branches is between 146A and 146B. The branches are rough in texture and they bear some large prickles which are of similar shape to the large prickles on the major stems. The prickles are about 0.6 to about 0.8 cm. in length. Prickle color is between 152B and 152C often lightly suffused with between 187C and 187D. The branches bear some small prickles of similar shape and coloration with sometimes few stipitate glands.

The color of the new shoots is between 146B and 146A often lightly suffused with between 187C and 187B. The new shoots are rough in texture and they bear some large prickles which are of similar size and shape to the large prickles on the branches; prickle color is between 152B and 152C often moderately suffused with between 187C and 187D. The shoots bear some small prickles of similar shape and coloration with sometimes few stipitate glands.

I claim:

1. A new and distinct *Floribunda* rose plant of the variety substantially as described and illustrated herein.

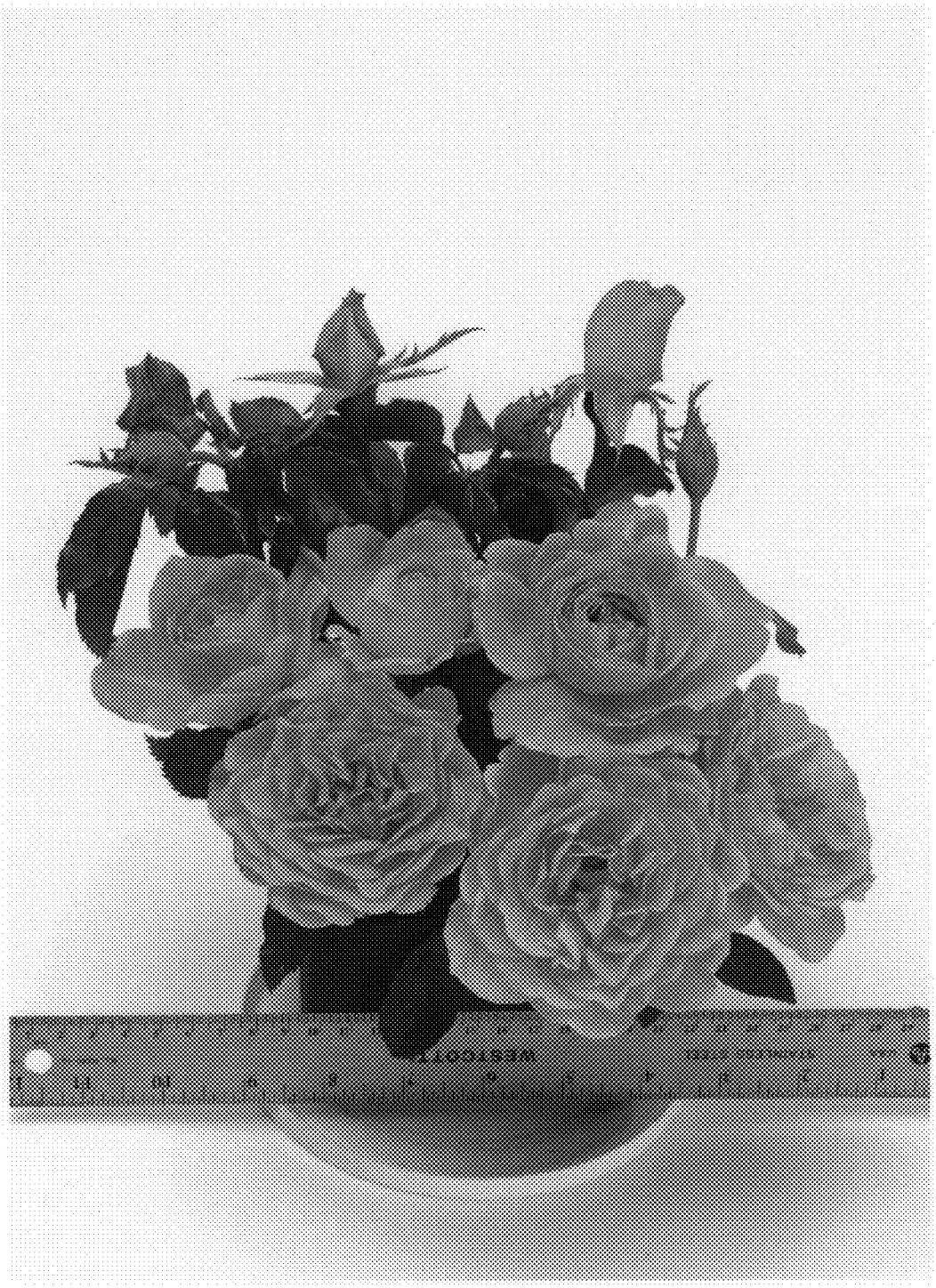

* * * * *